United States Patent [19]
Lambert et al.

[11] Patent Number: 6,159,976
[45] Date of Patent: Dec. 12, 2000

[54] POLYMORPH OF ZOPOLRESTAT MONOHYDRATE

[75] Inventors: John F. Lambert, North Stonington; Timothy Norris, Gales Ferry, both of Conn.

[73] Assignee: Pfizer Inc., New York, N.Y.

[21] Appl. No.: 09/374,729

[22] Filed: Aug. 13, 1999

Related U.S. Application Data

[60] Provisional application No. 60/097,474, Aug. 21, 1998.
[51] Int. Cl.[7] .................... A61K 31/502; C07D 237/30
[52] U.S. Cl. .................... 514/248; 514/248; 544/239
[58] Field of Search .................... 544/239; 514/248

[56] References Cited

U.S. PATENT DOCUMENTS

| | | | |
|---|---|---|---|
| 4,748,280 | 5/1988 | Mylari et al. | 568/595 |
| 4,868,301 | 9/1989 | Mylari et al. | 544/237 |
| 4,904,782 | 2/1990 | Sinay, Jr. et al. | 544/237 |
| 4,939,140 | 7/1990 | Larson et al. | 514/222 |
| 4,954,629 | 9/1990 | Mylari et al. | 544/237 |

FOREIGN PATENT DOCUMENTS

| | | |
|---|---|---|
| WO92/03432 | 3/1992 | WIPO . |
| WO9203432 | 3/1992 | WIPO . |

OTHER PUBLICATIONS

Mylari et al. Novel, Potent Aldose Reductase Inhibitors: 3,4–Dihydro–4–oxo–3[5–trifluoromethyl)–2–benzo-thiazolyl]methyl]–1–phthalazine–acetic Acid (Zopolrestat) and Congeners, J. Med. Chem., 34, pp. 108–122, 1991.

Mylari et al., J. Med. Chem., 1991, 34, 108–122.

*Primary Examiner*—Mukund J. Shah
*Assistant Examiner*—Ben Schroeder
*Attorney, Agent, or Firm*—Peter C. Richardson; Gregg C. Benson; Gabriel L. Kleiman

[57] ABSTRACT

This invention relates to zopolrestat monohydrate and polymorphs thereof. This invention also relates to processes for preparing zopolrestat monohydrate, for preparing polymorphs thereof and for preparing anhydrous zopolrestat. This invention also relates to compositions comprising zopolrestat monohydrate and to methods of using zopolrestat monohydrate and compositions thereof to treat diabetic complications such as diabetic cataracts, diabetic retinopathy or diabetic neuropathy, lower blood lipid levels or blood uric level.

26 Claims, No Drawings

POLYMORPH OF ZOPOLRESTAT MONOHYDRATE

This application is filed claiming priority from co-pending Provisional Application No. 60/097,474 filed Aug. 21, 1998.

BACKGROUND OF THE INVENTION

This invention relates to zopolrestat monohydrate, polymorphs thereof and to processes for preparing the polymorphs. This invention further relates to processes for using the polymorphs to prepare anhydrous zopolrestat, and to methods of using the polymorphs and to compositions comprising the polymorph to treat, prevent or reverse complications arising from diabetes mellitus. Zopolrestat, also known as 3,4-dihydro-4-oxo-3-((5-trifluoromethyl)-2-benzothiazolyl) methyl-1-phthalazineacetic acid, is the compound of formula I:

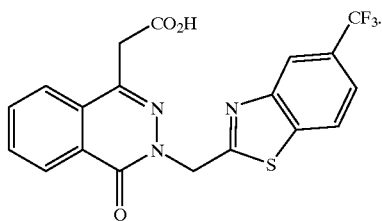

Zopolrestat is disclosed in U.S. Pat. No. 4,939,140 together with its utility in inhibition of aldose reductase, more specifically having utility in the treatment of complications arising from diabetes mellitus such as diabetic cataracts, retinopathy and neuropathy. Subsequently, zopolrestat has been disclosed as having utility in lowering blood lipid levels (U.S. Pat. No. 5,391,551) and in lowering blood uric acid levels (U.S. Pat. No. 5,064,830).

SUMMARY OF THE INVENTION

This invention provides a polymorph of zopolrestat monohydrate and processes for preparation therefor. Use of the instant polymorph of zopolrestat monohydrate allows for a faster filtration process and an improved production cycle for zopolrestat monohydrate This invention also provides the polymorph having the characteristic x-ray powder diffraction pattern set forth in Table 1 below.

This invention further provides processes for preparing the polymorph hereafter referred to as "Methods A and B".

Method A comprises:
(a) reacting 3,4-dihydro-4-oxo-3-((5-trifluoromethyl)-2-benzothiazolyl) methyl)-1-phthalazineacetic acid ethyl ester (hereafter referred to as "zopolrestat ethyl ester") with aqueous sodium hydroxide in a reaction inert polar solvent to form a first solution comprising sodium 3,4-dihydro-4-oxo-3-((5-(trifluoromethyl)-2-benzothiazolyl)methyl)-1-phthalazineacetate;
(b) adjusting said first solution to a pH of from about 7.5 to about 8.5 to form a second solution comprising sodium 3,4-dihydro-4-oxo-3-((5-(trifluoromethyl)-2-benzothiazolyl)methyl)-1-phthalazineacetate;
(c) adding to said second solution a suitable water soluble solvent to form a third solution comprising sodium 3,4-dihydro-4-oxo-3-((5-(trifluoromethyl)-2-benzothiazolyl)methyl)-1-phthalazineacetate; and
(d) adjusting said third solution to a pH of from about 1.5 to about 2.5 with a strong inorganic acid such as concentrated aqueous hydrochloric acid to form a solution of said polymorph.

A particularly preferred process within Method A comprises the additional subsequent step of filtering said solution of said polymorph to obtain solid 3,4-dihydro-4-oxo-3-((5-(trifluoromethyl)-2-benzothiazolyl)methyl)-1-phthalazineacetic acid monohydrate.

A still more particularly preferred process within the process of the immediately preceding paragraph comprises a process wherein said suitable water soluble solvent in step (c) is ethyl acetate, a $(C_1-C_6)$alkanol or tetrahydrofuran.

Method B comprises:
(a) reacting anhydrous 3,4-dihydro-4-oxo-3-((5-trifluoromethyl)-2-benzothiazolyl)methyl)-1-phthalazineacetic acid (hereafter referred to as "anhydrous zopolrestat") with aqueous sodium hydroxide in a reaction inert polar solvent to form a first solution comprising sodium 3,4-dihydro-4-oxo-3-((5-(trifluoromethyl)-2-benzothiazolyl)methyl)-1-phthalazineacetate;
(b) adjusting said first solution to a pH of from about 7.5 to about 8.5 to form a second solution comprising sodium 3,4-dihydro-4-oxo-3-((5-(trifluoromethyl)-2-benzothiazolyl)methyl)-1-phthalazineacetate;
(c) adding to said second solution a suitable water soluble solvent to form third solution comprising sodium 3,4-dihydro-4-oxo-3-((5-trifluoromethyl)-2-enzothiazolyl)methyl)-1-phthalazineacetate (hereafter referred to as "zopolrestat sodium carboxylate"); and
(d) adjusting said third solution to a pH of from about 1.5 to about 2.5 with a strong inorganic acid such as concentrated aqueous hydrochloric acid to form a solution of said polymorph.

A particularly preferred process within Method B comprises the additional subsequent step of filtering said solution of said polymorph to obtain solid 3,4-dihydro-4-oxo-3-((5-(trifluoromethyl)-2-benzothiazolyl)methyl)-1-phthalazineacetic acid monohydrate.

A still more particularly preferred process within the process of the immediately preceding paragraph comprises a process wherein said suitable water soluble solvent in step (c) is ethyl acetate, a $(C_1-C_6)$alkanol or tetrahydrofuran.

This invention also provides a process for preparing anhydrous zopolrestat comprising recrystallizing a zopolrestat monohydrate polymorph from a mixture of a water soluble solvent and water. Preferred water soluble solvents include ethyl acetate, a $(C_1-C_6)$alkanol and tetrahydrofuran. It is particularly preferred that the ratio of ethyl acetate to water is from 1:4 to 1:12; the ratio of a $(C_1-C_6)$alkanol to water is from 1:0.85 to 1:1.15 and the ratio of tetrahydrofuran to water is from 1:0.85 to 1:1.15.

This invention further provides a process for preparing anhydrous zopolrestat comprising drying a polymorph of zopolrestat monohydrate, optionally heating the polymorph in water prior to drying.

Also, included in the invention is a method of treating diabetic cardiomyopathy in a human subject in need of such treatment comprising administering a therapeutically effective amount of zopolrestat monohydrate to said subject, a method of reducing non-cardiac tissue damage resulting from ischemia comprising administering to a mammal in need of such treatment an amount of zopolrestat monohydrate effective at reducing non-cardiac ischemic damage, a method of lowering blood uric acid levels in a mammal in need of such lower levels comprising administering to said mammal a blood uric acid level lowering amount of zopolrestat monohydrate, a method of lowering blood lipid levels in a human comprising administering to a human in need of such treatment an effective amount of zopolrestat monohydrate, a method of inhibiting aldose reductase activity in a diabetic subject comprising administering to said diabetic subject an effective amount of zopolrestat monohydrate, a method of treating or preventing anginal pain by direct action on the myocardium in a mammal comprising administering to said mammal a therapeutically effective amount of zopolrestat monohydrate, a method of preventing heart damage resulting from myocardial ischemia in a mammal comprising administering to said mammal a therapeutically effective amount of zopolrestat monohydrate, and a method of treating diabetic nephropathy in a mammal in need of such treatment comprising administering to said mammal a therapeutically effective amount of zopolrestat monohydrate.

This invention is also directed to a pharmaceutical composition comprising zopolrestat monohydrate and a pharmaceutically acceptable carrier or diluent.

This invention also includes a pharmaceutical composition for inhibiting aldose reductase comprising zopolrestat monohydrate and a pharmaceutically acceptable carrier or diluent.

This invention further includes a pharmaceutical composition for treating, preventing or reversing complications from diabetes mellitus comprising zopolrestat monohydrate and a pharmaceutically acceptable carrier or diluent.

DETAILED DESCRIPTION OF THE INVENTION

In this specification and the appendant claims, the term "polymorph" means a form of a substance in which the substance displays different forms, preferably in a solution.

In this specification the term "$C_1$–$C_6$ alkanol" means $C_1$–$C_6$ alkyl-OH including branched and straight chain alkyl groups such as, but not limited to, methanol, ethanol, n-propanol, iso-propanol, n-butanol, iso-butanol, tert-butanol, n-pentanol or n-hexanol.

In this specification the phrase "room temperature" means about 25° C.

In this specification, the expression "reaction inert solvent" refers to a solvent or mixture of solvents which does not interact with starting materials, reagents, intermediates or products in a manner which adversely affects the yield of the desired product.

Zopolrestat monohydrate can be prepared by the following methods.

According to Method A (a) of this invention, zopolrestat sodium carboxylate can be obtained through a process comprising slurrying zopolrestat ethyl ester in a reaction inert polar solvent followed by reaction with aqueous sodium hydroxide. The suitable reaction inert polar solvent may be a $C_1$–$C_6$ alkanol or tetrahydrofuran (THF) and is preferably ethanol. Formation of the slurry can be performed at a temperature in the range of 10° to 60° C., preferably at room temperature. The slurry thus obtained is added to aqueous sodium hydroxide to form a reaction mixture which is stirred at a temperature in the range of 10° to 60° C., preferably 30° to 40° C., for about 30 minutes to 12 hours, preferably 2 to 4 hours. Zopolrestat sodium carboxylate thus obtained can optionally be filtered according to procedures well known to those skilled in the art.

Alternatively, zopolrestat sodium carboxylate can be obtained by Method B (a) of this invention. According to Method B (a), anhydrous zopolrestat is reacted with aqueous sodium hydroxide in a reaction inert polar solvent such as a $C_1$–$C_6$ alkanol THF. A preferred reaction inert polar solvent is ethanol. The volume ratio of the reaction inert polar solvent to water ranges from 6:1 to 0.5:1. Preferably the volume ratio is 1:1. The reaction is carried out at a temperature in the range of 10° to 60° C., preferably at room temperature, at a pH in the range of from about 10 to about 14, preferably about 11, for from about 30 minutes to 12 hours. The zopolrestat sodium carboxylate may be isolated according to procedures well known to those skilled in the art.

The zopolrestat sodium carboxylate solution obtained by either Method A (a) or B (a) is treated with an acid until the pH of the solution is adjusted to a pH from about 7.5 to about 8.5, preferably a pH from about 7.8 to about 8.2. A suitable acid is a strong inorganic acid such as hydrochloric acid, hydrobromic acid or sulfuric acid, preferably hydrochloric acid.

A suitable organic solvent is added to the solution obtained. Suitable organic solvents are water soluble solvents, for example, esters such as ethyl acetate, or ($C_1$–$C_6$)alkanols such as methanol, THF or ethanol. A preferable solvent is ethyl acetate.

The pH of the obtained solution is adjusted to a pH from about 1.5 to about 2.5, preferably to about pH 2 with a suitable acid to crystallize zopolrestat monohydrate polymorph in slurry form. The suitable acid is a strong inorganic acid such as concentrated aqueous hydrochloric acid, hydrobromic acid or sulfuric acid, preferably concentrated aqueous hydrochloric acid. This crystallization may be performed at a temperature in the range of 5° to 60° C., preferably 20° to 35° C.

The slurry of zopolrestat monohydrate polymorph thus obtained is filtered and washed with a suitable solvent such as a ($C_1$–$C_6$)alkanol, ester, water or a mixture thereof.

In a preferred embodiment of this invention, recrystallization of zopolrestat monohydrate to prepare anhydrous zopolrestat is carried out in a solvent comprising a water soluble solvent and water such as ethyl acetate and water, a ($C_1$–$C_6$)alkanol and water or THF and water.

The preferred solvents are those comprising ethyl acetate and water at a ratio of from 1:4 to 1:12, and a ($C_1$–$C_6$) alkanol and water or THF and water at a ratio of from 1:0.85 to 1:1.15. The more preferred solvents are those comprising ethyl acetate and water at a ratio of from 1:7 to 1:9, and a ($C_1$–$C_6$)alkanol and water or THF and water at a ratio of from 1:0.95 to 1:1.05. An even more preferred solvent is a solvent comprising ethyl acetate and water at a ratio of 1:8.

A zopolrestat monohydrate polymorph of this invention can be converted to the anhydrous form by drying. The polymorph can be dried in a drying apparatus such as drying oven at a temperature from about 40° to about 90° C., at atmospheric pressure or under vacuum, until the water is substantially removed (i.e., until at the water concentration of about 0%). The water concentration may be measured by a known technique such as Karl Fischer method. A zopolrestat monohydrate polymorph of this invention may be heated in water prior to drying. A ratio of the polymorph and water of the mixture is from about 1:1 to about 1:10. The mixture is heated at from about 70° C. to the refluxing temperature of the mixture for from about 30 minutes to 6 hours. A preferable heating temperature is about 90° C. The mixture may be stirred while heating.

Filtering procedures known for those skilled in the art can be used in the processes disclosed above. The filtrations can be performed by centrifugation, or using Buchner style filter, Rosenmund filter or plates and frame press, preferably Buchner style filter, Rosenmund filter or plates and frame press are used.

Anhydrous zopolrestat and zopolrestat ethyl ester can be prepared according to known procedure (e.g., B. L. Mylari et al., J. Med. Chem., 1991, 34, 108–122). For example, zopolrestat ethyl ester is prepared by contacting or reacting 3-(cyanomethyl)-3,4-dihydro-4-oxo-1-phthalazine acetic acid, ethyl ester with 2-amino-4-(trifluoromethyl) benzenethiol, hydrochloride. The reaction is carried out in a reaction inert solvent such as ethanol at about the reflux temperature of the reaction mixture for from about 1 to 12 hours. The ester thus obtained is hydrolyzed by treating the ester with sodium or potassium hydroxide in an alkanol such as methanol followed by treatment with a mineral acid such as hydrochloric acid in water.

The polymorph of zopolrestat monohydrate thus obtained is novel and useful in the manufacture of zopolrestat. Said polymorph shortens the time required to carry out the overall process by speeding up the filtration process.

Zopolrestat monohydrate and polymorphs thereof thus obtained have utility in the treatment of complications arising from diabetes mellitus such as diabetic cataracts, retinopathy and neuropathy. More specifically, zopolrestat monohydrate and polymorphs thereof are useful for treatment comprising reversal of diabetic cardiomyopathy, reducing damage of tissue in brain, liver, kidney, lung, gut, skeletal muscle, or pancreas, retinal tissue or intestinal tissue, more specifically in human, particularly in a human having diabetes.

A therapeutically effective amount of zopolrestat monohydrate and polymorphs thereof of this invention can be administered to a human subject. Such administration comprises any known method for therapeutically providing an active compound to a human subject including such conventional routes as oral, transdermal, intraduodenal, or parenteral administration. For purposes of the method of the present invention, oral administration is generally preferred. In carrying out the objectives of the method of this invention, an amount of a compound of this invention that is effective for treating or reversing the particular condition is employed. Typically, an effective dose for the a compound of this invention is in the range of from about 0.1 mg per day to about 1,000 mg per day in either single (e.g., once-daily) or multiple doses. Preferred dosage ranges for a compound of this invention is from about 250 mg per day to about 1,000 mg per day in a single, oral dose. However, some variation in dosage will be necessary depending upon the condition of the patient being treated. In any event, the person responsible for administration will determine the appropriate dosage amount for the individual subject requiring treatment.

A compound of this invention is employed either alone, together in combination with another aldose reductase inhibitor or in combination with a pharmaceutically acceptable carrier. Suitable carriers may include solid diluents or fillers, sterile aqueous solutions and various physiologically compatible organic solvents. The pharmaceutical compositions formed by combining the active compound and the pharmaceutically acceptable carriers are then readily administered in a variety of dosage forms such as tablets, powders, lozenges, syrups, injectable solutions and so forth. These pharmaceutical compositions may, if desired, contain additional ingredients such as flavorings, binders, excipients, and the like. For purposes of the preferred route of oral administration, tablets containing various excipients such as sodium citrate, calcium carbonate and calcium phosphate may be used along with various disintegrants such as starch, alginic acid and certain complex silicates, together with binding agents such as polyvinylpyrrolidone, sucrose, gelatin, and acacia. Additionally, lubricating agents such as magnesium stearate, sodium lauryl sulfate, and talc are often useful for tabletting purposes. Solid compositions of a similar type may also be used as fillers in soft and hard filled gelatin capsules. Preferred materials for this use include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and various combinations thereof.

For parenteral administration, solutions of the compound useful in this invention, in sesame or peanut oil, aqueous propylene glycol, or in aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Anhydrous zopolrestat obtained by drying zopolrestat monohydrate or polymorph thereof of this invention can be used for inhibiting aldose reductase, more specifically in the treatment of complications arising from diabetes mellitus such as diabetic cataracts, retinopathy and neuropathy. The anhydrous zopolrestat can be administered to a human in a similar manner as described above or disclosed, for example, in U.S. Pat. No. 4,939,140.

EXAMPLES AND EXPERIMENTAL

The present invention is illustrated by the following examples. It will be understood, however, that the invention is not limited to the specific details of these examples.

Example 1

Anhydrous zopolrestat (20 g, 0.048 mole), ethanol (90 ml) and water (90 ml) were stirred at room temperature in a reaction flask. Aqueous 50% sodium hydroxide solution was slowly added to the crystal slurry until a pale yellow solution was formed at about pH 11.0. In this example 2.6 ml of aqueous 50% sodium hydroxide was used. One drop of concentrated hydrochloric acid was added to the pale yellow solution so that the pH fell to 7.8. Ethyl acetate (22.5 ml) was added to the solution at pH 7.8. Concentrated hydrochloric acid was added to lower the pH of the solution to 2. Crystallization initiated and a thick white slurry that could be stirred was obtained at 27° C. The slurry was cooled to 5° C., granulated for a period and the crystals were isolated by filtration and washed with a solution mixture of ethanol (18 ml), water (18 ml) and ethyl acetate (4.5 ml). The product was air dried to give crystals of zopolrestat monohydrate product, 21 g, 100% with a characteristic X-ray diffraction pattern set forth in Table 1. m.p. 188–190° C., water content 4.1% by Karl Fischer method (theory 4.1%).

Example 2

Zopolrestat ethyl ester (50 g, 0.11 mole) and ethanol (200 ml) were stirred at room temperature in a reaction flask to form a white crystal slurry. Sodium hydroxide (15.11 g, 0.38 mole) and water (200 ml) were mixed with cooling to form a solution of aqueous sodium hydroxide. The sodium hydroxide solution was added to the white crystal slurry and the resultant mixture was stirred in the temperature range 30°–40° C. After a period of 2–4 hours, a red/purple solution was formed. This indicated that the reaction had proceeded to completion. The solution was filtered and treated with concentrated hydrochloric acid until the pH was adjusted to 8.1. In this example, 20 ml of concentrated HCl were required to effect the pH adjustment. Ethyl acetate was added to the solution at pH 8.1. The pH was then adjusted to pH 2 by addition of a further quantity of concentrated hydrochloric acid (10.5 ml). Crystallization initiated and a thick white slurry was obtained at 33–28° C.

The slurry was cooled to 5° C., granulated for a period and the crystals were isolated by filtration and washed with a solution mixture of ethanol (50 ml), water (50 ml) and ethyl acetate (12.5 ml). The product was air dried to give crystals of zopolrestat monohydrate product, 41.4 g, 88% with a characteristic X-ray diffraction pattern set forth in Table 1. m.p. 188–190° C., water content 4.1% by Karl Fischer method (theory 4.1%).

X-ray diffraction pattern of zopolrestat monohydrate polymorph of this invention prepared in Examples 1 and 2 were measured with Siemens D5000, X-ray diffractometer under the following conditions:

| | |
|---|---|
| Anode: | Cu; |
| Wavelength 1: | 1.54056 |
| Wavelength 2: | 1.54439 |
| Rel Intensity: | 0.500 |
| Range #1 | |
| Coupled: | 3.000 to 40.000 |
| Step Size: | 0.040 |
| Step Time: | 1.00 |
| Smoothing Width: | 0.300 |
| Threshold: | 1.0 |

The x-ray diffraction pattern thus measured is summarized in Table 1.

TABLE 1

| 2-theta | d/A | 2-theta | d/A | 2-theta | d/A |
|---|---|---|---|---|---|
| 5.3 | 16.7 | 17.6 | 5.0 | 26.2 | 3.4 |
| 5.9 | 15.1 | 19.2 | 4.6 | 27.3 | 3.3 |
| 8.0 | 11.0 | 20.1 | 4.4 | 28.3 | 3.2 |
| 10.5 | 8.4 | 21.2 | 4.2 | 29.0 | 3.1 |
| 11.8 | 7.5 | 21.4 | 4.2 | 29.5 | 3.0 |
| 12.3 | 7.2 | 22.1 | 4.0 | 30.2 | 3.0 |
| 12.6 | 7.0 | 22.5 | 4.0 | 30.9 | 2.9 |
| 13.1 | 6.8 | 23.1 | 3.8 | 31.7 | 2.8 |
| 14.3 | 6.2 | 23.4 | 3.8 | 32.6 | 2.7 |
| 15.7 | 5.6 | 23.8 | 3.7 | 33.4 | 2.7 |
| 16.5 | 5.4 | 24.3 | 3.7 | 36.6 | 2.5 |
| 17.1 | 5.2 | 25.3 | 3.5 | | |

What is claimed is:

1. The polymorph of 3,4-dihydro-4-oxo-3-((5-(trifluoromethyl)-2-benzothiazolyl)methyl)-1-phthalazineacetic acid monohydrate having the following characteristic x-ray powder diffraction pattern:

| 2-theta | d/A | 2-theta | d/A | 2-theta | d/A |
|---|---|---|---|---|---|
| 5.3 | 16.7 | 17.6 | 5.0 | 26.2 | 3.4 |
| 5.9 | 15.1 | 19.2 | 4.6 | 27.3 | 3.3 |
| 8.0 | 11.0 | 20.1 | 4.4 | 28.3 | 3.2 |
| 10.5 | 8.4 | 21.2 | 4.2 | 29.0 | 3.1 |
| 11.8 | 7.5 | 21.4 | 4.2 | 29.5 | 3.0 |
| 12.3 | 7.2 | 22.1 | 4.0 | 30.2 | 3.0 |
| 12.6 | 7.0 | 22.5 | 4.0 | 30.9 | 2.9 |
| 13.1 | 6.8 | 23.1 | 3.8 | 31.7 | 2.8 |
| 14.3 | 6.2 | 23.4 | 3.8 | 32.6 | 2.7 |
| 15.7 | 5.6 | 23.8 | 3.7 | 33.4 | 2.7 |
| 16.5 | 5.4 | 24.3 | 3.7 | 36.6 | 2.5 |
| 17.1 | 5.2 | 25.3 | 3.5 | | |

2. A process for preparing the polymorph of claim 1 comprising:
   (a) reacting 3,4-dihydro-4-oxo-3-((5-trifluoromethyl)-2-benzothiazolyl)methyl)-1-phthalazineacetic acid ethyl ester with aqueous sodium hydroxide in a reaction inert polar solvent to form a first solution comprising sodium 3,4-dihydro-4-oxo-3-((5-(trifluoromethyl)-2-benzothiazolyl)methyl)-1-phthalazineacetate;
   (b) adjusting said first solution to a pH of from about 7.5 to about 8.5 to form a second solution comprising sodium 3,4-dihydro-4-oxo-3-((5(trifluoromethyl)-2-benzothiazolyl)methyl)-1-phthalazineacetate;
   (c) adding to said second solution a suitable water soluble solvent to form a third solution comprising sodium 3,4-dihydro-4-oxo-3-((5-trifluoromethyl)-2-benzothiazolyl)methyl)-1-phthalazineacetate; and
   (d) adjusting said third solution to a pH of from about 1.5 to about 2.5 with a strong inorganic acid to form a solution of said polymorph.

3. A process of claim 2 comprising the additional subsequent step of filtering said solution of said polymorph to obtain solid 3,4-dihydro-4-oxo-3-((5-(trifluoromethyl)-2-benzothiazolyl)methyl)-1-phthalazineacetic acid monohydrate.

4. A process of claim 3 wherein said suitable water soluble solvent in step (c) is ethyl acetate, a ($C_1$–$C_6$)alkanol or tetrahydrofuran.

5. A process for preparing the polymorph of claim 1 comprising:
   (a) reacting anhydrous 3,4-dihydro-4-oxo-3-((5-trifluoromethyl)-2-benzothiazolyl)methyl)-1-phthalazineacetic acid with aqueous sodium hydroxide in a reaction inert polar solvent to form a first solution comprising sodium 3,4-dihydro-4-oxo-3-((5-(trifluoromethyl)-2-benzothiazolyl)methyl)-1-phthalazineacetate;
   (b) adjusting said first solution to a pH of from about 7.5 to about 8.5 to form a second solution comprising sodium 3,4-dihydro-4-oxo-3-((5-(trifluoromethyl)-2-benzothiazolyl) methyl)-1-phthalazineacetate;
   (c) adding to said second solution a suitable water soluble solvent to form a third solution comprising sodium 3,4-dihydro-4-oxo-3-((5-trifluoromethyl)-2-benzothiazolyl)methyl)-1-phthalazineacetate; and
   (d) adjusting said third solution to a pH of from about 1.5 to about 2.5 with a strong inorganic acid to form a solution of said polymorph.

6. A process of claim 5 comprising the additional subsequent step of filtering said solution of said polymorph to obtain solid 3,4-dihydro-4-oxo-3-((5-(trifluoromethyl)-2-benzothiazolyl)methyl)-1-phthalazineacetic monohydrate.

7. A process of claim 6 wherein said suitable water soluble solvent in step (c) is ethyl acetate, a $(C_1-C_6)$alkanol or tetrahydrofuran.

8. A process for preparing anhydrous 3,4-dihydro-4-oxo-3-((5(trifluoromethyl)-2-benzothiazolyl)methyl)-1-phthalazineacetic acid comprising recrystallizing 3,4-dihydro-4-oxo-3-((5-(trifluoromethyl)-2-benzothiazolyl)methyl)-1-phthalazineacetic monohydrate from a mixture of a water soluble solvent and water.

9. A process of claim 8 wherein said water soluble solvent is ethyl acetate, a $C_1-C_6$ alkanol or tetrahydrofuran.

10. A process of claim 9 wherein the ratio of ethyl acetate to water is from 1:4 to 1:12, the ratio of a $(C_1-C_6)$alkanol to water is from 1:0.85 to 1:1.15 and the ratio of tetrahydrofuran to water is from 1:0.85 to 1:1.15.

11. A process for preparing anhydrous 3,4-dihydro-4-oxo-3-((5-(trifluoromethyl)-2-benzothiazolyl)methyl)-1-phthalazineacetic acid comprising drying the polymorph of claim 1.

12. A process of claim 11 comprising heating the polymorph in water prior to drying.

13. A method of treating diabetic cardiomyopathy in a human subject in need of such treatment comprising administering a therapeutically effective amount of a compound of claim 1 to said subject.

14. A method of claim 13 wherein said treatment comprises reversal of said diabetic cardiomyopathy.

15. A method of reducing non-cardiac tissue damage resulting from ischemia comprising administering to a mammal in need of such treatment an amount of a compound of claim 1 effective at reducing non-cardiac ischemic damage.

16. A method of claim 15 wherein said tissue is brain, liver, kidney, lung, gut, skeletal muscle, spleen, pancreas, retinal tissue or intestinal tissue.

17. A method of claim 16 wherein said mammal is a human.

18. A method of claim 17 wherein said human has diabetes.

19. A method of lowering blood uric acid levels in a mammal in need of such lower levels comprising administering to said mammal a blood uric acid level lowering amount of a compound of claim 1.

20. A method of lowering blood lipid levels in a human comprising administering to a human in need of such treatment an effective amount of a compound of claim 1.

21. A method of inhibiting aldose reductase activity in a diabetic subject comprising administering to said diabetic subject an effective amount of a compound of claim 1.

22. A method of treating anginal pain by direct action on the myocardium in a mammal comprising administering to said mammal a therapeutically effective amount of a compound of claim 1.

23. A method of treating diabetic nephropathy in a mammal in need of such treatment comprising administering to said mammal a therapeutically effective amount of a compound of claim 1.

24. A pharmaceutical composition comprising a compound of claim 1 and a pharmaceutically acceptable carrier or diluent.

25. A pharmaceutical composition for inhibiting aldose reductase comprising a compound of claim 1 and a pharmaceutically acceptable carrier or diluent.

26. A pharmaceutical composition for treating or reversing complications arising from diabetes mellitus comprising a compound of claim 1 and a pharmaceutically acceptable carrier or diluent.

* * * * *